United States Patent [19]

Gatfield et al.

[11] 4,451,565
[45] May 29, 1984

[54] ENZYME-MEDIATED SYNTHESIS OF ESTERS AND LACTONES

[75] Inventors: Ian Gatfield, Hoexter; Theodor Sand, Holzminden, both of Fed. Rep. of Germany

[73] Assignee: Haarmann & Reimer GmbH, Holzminden, Fed. Rep. of Germany

[21] Appl. No.: 350,519

[22] Filed: Feb. 19, 1982

[30] Foreign Application Priority Data

Mar. 10, 1981 [DE] Fed. Rep. of Germany ........ 3108927

[51] Int. Cl.³ .......................... C12P 17/00; C12P 7/00; C12P 7/62; C12R 1/785
[52] U.S. Cl. .................................... 435/117; 435/132; 435/135; 435/931
[58] Field of Search ................ 435/117, 132, 135, 931

[56] References Cited

FOREIGN PATENT DOCUMENTS 7008787 1/1982 Japan .................................. 435/135

OTHER PUBLICATIONS

Moskowitz et al.: J. Agric. Food Chem. 25, 1146 (1977).
Chemical Abstracts, vol. 91, 1979 p. 609.
Chemical Abstracts, vol. 87, 1977 p. 440.
Patent Abstracts (Japan), vol. 5, No. 89, Jun. 10, 1981.

*Primary Examiner*—Thomas G. Wiseman
*Assistant Examiner*—James Martinell
*Attorney, Agent, or Firm*—Sprung, Horn, Kramer & Woods

[57] ABSTRACT

In the enzyme-mediated synthesis of an ester or lactone from at least one carboxylic acid of the formula $$R-CH_2-CH_2-COOH$$

wherein
R is a hydrogen atom, or a hydrocarbon radical which has 1 to 21 carbon atoms and which can be optionally substituted by hydroxyl groups or alkoxy groups with 1 to 10 carbon atoms, with at least one primary or secondary alcohol having 1 to 15 carbon atoms, the improvement which comprises employing as the enzyme the esterase from Mucor miehei and effecting the synthesis in the absence of water. Advantageously, the synthesis is effected at about room temperature, the mol ratio of carboxylic acid to alcohol is from about 1:1 to 1:1.1, and the enzyme is used in a quantity of about 3 to 20% by weight of the carboxylic acid. The absence of water facilitates recovery, as by distillation.

5 Claims, No Drawings

ENZYME-MEDIATED SYNTHESIS OF ESTERS AND LACTONES

The present invention relates to a process for the enzymatic synthesis of esters and lactones.

A process for the preparation of terpene alcohol esters by the reaction of terpene alcohols with fatty acids in the presence of selected lipases is described in Japanese Patent Application No. 54,041,385. In contrast to the customary procedure for reacting carboxylic acids with alcohols, namely in the presence of a strong acid at elevated temperatures, the enzymatic esterification proceeds with high yields, under mild conditions, at room temperature and in the absence of strong acids. The large quantity of water, namely ten to twenty times the weight of the carboxylic acid employed, which is essential for the activation of these lipases, is on the other hand disadvantageous, reducing the rate of reaction and causing difficulties in the work-up. Very surprisingly, it has been found that if the esterase from Mucor miehei is used as the enzyme, the esterification proceeds very satisfactorily under non-aqueous conditions.

The invention therefore relates to a process for the enzymatic synthesis of esters and lactones from carboxylic acids or mixtures of carboxylic acids of the general formula

$$R-CH_2-CH_2-COOH \qquad (I)$$

wherein

R represents a hydrogen atom or a straight-chain or branched, saturated or unsaturated hydrocarbon radical which has 1 to 21 carbon atoms and which can optionally be substituted by hydroxyl groups or alkoxy groups with 1 to 10 carbon atoms, and primary and secondary alcohols having 1 to 15 carbon atoms, characterized in that the reaction is effected in the presence of the esterase from Mucor miehei and in the absence of water.

The esterase is obtained from Mucor miehei by fermentation (data sheet of Rapidase, Seclin/France). It is a lipase with esterase activity, and is commercially obtainable, for example as esterase 30,000 of Messrs Rapidase, for the hydrolysis of vegetable and animal fats.

Saturated fatty acids, such as propionic acid, butyric acid, caproic acid, caprylic acid, capric acid, lauric acid, myristic acid, palmitic acid, stearic acid and arachic acid, unsaturated fatty acids, such as dec-9-enoic acid, oleic acid, linoleic acid, linolenic acid and arachidonic acid, branched fatty acids, such as isopalmitic acid (14-methyl-pentadecanoic acid), and hydroxyl-substituted carboxylic acids, such as 4-hydroxybutyric acid and 15-hydroxy-pentadecanoic acid, are particularly suitable as the carboxylic acids of the general formula I. The latter acids form lactones under the reaction conditions.

The carboxylic acids can be employed as the pure compounds, or also as mixtures, as produced in the hydrolysis of natural fats, such as, for example, butter fat.

Saturated and unsaturated, branched and unbranched alcohols having 1 to 15 carbon atoms, such as methanol, ethanol, propan-1-ol, propan-2-ol, butan-1-ol, butan-2-ol, isobutanol, hex-3-en-1-ol, hex-2-en-1-ol, hexan-1-ol, oct-7-en-1-ol and oct-3-en-1-ol, as well as terpene alcohols and sesquiterpene alcohols, such as geraniol, nerol, citronellol, farnesol, etc., are examples of suitable alcohols.

The carboxylic acids and alcohols are employed in a molar ratio of about 2:1 to 1:6, preferably in a molar ratio of about 1:1 to 1:1.1.

In the esterification of propionic acid and butyric acid, it can be advantageous, for increasing the reaction rate and the yield, to add a higher carboxylic acid or the ester of a higher carboxylic acid. Higher carboxylic acids are to be understood as meaning those having more than 5 carbon atoms, particularly those having 10 to 20 carbon atoms. The quantity of higher carboxylic acids should be about 0.5 to 2 mols, preferably about 1 mol, per mol of propionic acid or butyric acid.

As a rule, the reaction according to the invention can be carried out without a solvent. For the reaction of otherwise immiscible components and for increasing the stirrability and, in the preparation of lactones, for achieving a dilution effect, it can be advantageous to carry out the reaction in the presence of a solvent. Ethers, such as diethyl ether and tetrahydrofuran, and aromatic hydrocarbons, such as benzene and toluene, are suitable solvents.

The reaction is advantageously carried out in the temperature range from 0° to 50° C., preferably at room temperature.

The reaction time depends on the quantity used and on the activity of the esterase, and is in the region of 24 to 72 hours. However, particularly in the case of reaction mixtures which can easily be separated by distillation, it can be advantageous to terminate the reaction earlier, for example after 8 hours, when the conversion is about 40 to 60%, and to re-use the recovered starting materials.

The enzyme can be employed in pure form or on a carrier to which it is chemically or physically bound. The quantity of the enzyme, relative to the carboxylic acid employed, is about 1 to 30% by weight, preferably about 3 to 20% by weight, 3% by weight being sufficient in the case of pure higher carboxylic acids to achieve an economically acceptable reaction rate, while about 20% by weight is to be employed in the case of mixtures containing the lower carboxylic acid homologues.

After the end of the reaction, the esterase can be removed by suitable means, such as filtration or decantation, and can be re-used several times without detectable loss of activity.

While the conversion depends on the quantity and the activity of the esterase, as well as on the reaction time, the yield almost corresponds to the theoretical value, since the unreacted starting materials can be recovered unchanged and re-used. The course of the reaction is surprising, since it had previously been assumed that lipases exhibit enzyme activity only in aqueous media, including emulsions.

The lactones and esters according to the invention can be used as odor substances and/or flavor substances (Perfume and Flavour Chemicals, S. Arctander (1969).

EXAMPLES

Example 1

750 mg of esterase 30,000 (Messrs. Rapidase) are added to 5 g (56.8 mmols) of butyric acid and 35.0 g (227.3 mmols) of geraniol and the mixture is stirred for 72 hours at room temperature. The enzyme is then removed by filtration. A degree of esterification of 76.6% results from the determination of the acid number (18.2 mg of KOH/g) and the ester number (59.6 mg of KOH/g). The distillation of the reaction product yields gas chromatographically pure geranyl n-butyrate. Corresponding results are achieved if, instead of geraniol, nerol, citronellol and farnesol are employed.

Example 2

7.21 g (50 mmols) of caprylic acid and 15.4 g (100 mmols) of geraniol are reacted with 0.43 g of esterase 30,000, analogously to Example 1. The determination of the acid number and the ester number gives a degree of esterification of 89.8%. Distillation of the reaction product yields gas chromatographically pure geranyl caprylate.

Examples 3 to 5

Analogously to Example 1, various quantities of ethanol and 60 mg of esterase 30,000 are added to 2 g (7 mmols) of oleic acid and the mixture is stirred at room temperature. To determine the degree of esterification, samples are removed during the reaction period and the acid number and the ester number are determined. The results are summarized in Table I.

TABLE I

| Example | mmols of ethanol | Degree of esterification in % after | | | | | |
|---|---|---|---|---|---|---|---|
| | | 2.5 | 5 | 8 | 24 | 32 | 48 | 72 hours |
| 3 | 7 | 16.5 | 34.1 | 51.1 | 79.8 | 84.9 | 84.0 | 90.4 |
| 4 | 14 | 19.3 | 28.6 | 51.7 | 61.3 | 69.2 | 81.4 | 80.0 |
| 5 | 42 | 11.2 | 17.6 | 30.9 | 57.9 | 70.6 | 74.3 | 86.7 |

Example 6

2.8 g (10 mmols) of oleic acid and 2.96 g (40 mmols) of n-butanol are reacted with 60 mg of esterase 30,000, analogously to Example 1. A degree of esterification of 83.1% is obtained.

If, instead of n-butanol, the same quantity of sec.-butanol is employed, a degree of esterification of 84.2% is achieved.

Example 7

500 mg of esterase 30,000 are added to 5.6 g (20 mmols) of oleic acid and 2.68 g (20 mmols) of oct-3-en-1-ol, and the mixture is stirred for 72 hours at room temperature. The determination of the acid number and the ester number gives a degree of esterification of 90.0%.

Example 8

0.88 g (10 mmols) of butyric acid and 1.48 g (20 mmols) of n-butanol are stirred for 72 hours with 60 mg of esterase 30,000, analogously to Example 1. The determination of the acid number and the ester number gives a degree of esterification of 89.4%.

Example 9

0.26 g of esterase 30,000 is added to 1.3 g of a fatty acid mixture which had been obtained by the hydrolysis of butter fat, and 0.46 g of ethanol and the mixture is stirred for 72 hours at room temperature. The determination of the degree of esterification gives a value of 98.7%.

If, instead of ethanol, 0.74 g of isobutanol, 0.88 g of isoamyl alcohol or 0.6 g of n-propanol is employed, degrees of esterification of 87.6%, 85.6% and 86.2% result.

Example 10

6.3 g (50 mmols) of the sodium salt of 4-hydroxybutyric acid are dissolved in a little water, 50 ml of 1 N hydrochloric acid (50 mmols) are added to the solution while stirring and, after 30 minutes, the mixture is frozen and freeze-dried. 50 ml of toluene are added to the salt-containing product and the mixture is stirred for 72 hours at room temperature in the presence of 200 mg of esterase 30,000. The reaction mixture is then filtered, the solvent distilled off and the residue worked up by distillation. 0.6 g of γ-butyrolactone are obtained.

Example 11

4 g of oleic acid and 0.66 g of ethanol are stirred for 48 hours at room temperature with esterase 30,000. The reaction product is then separated off by decantation, oleic acid and ethanol are again added to the enzyme and the mixture is stirred for 48 hours at room temperature. This process is repeated a total of 11 times. During these repeated processes, the degree of esterification varies between 83.1 and 86.6%, and a decrease could not be observed.

Example 12

A solution of 1.3 g of esterase 30,000 in 60 ml of water is shaken for 3 hours with 15 g of a weak cation exchanger based on polystyrene. The supernatant liquid is removed by filtration and the ion exchanger is freed from excess enzyme by washing with water and then freed from water by washing with absolute ethanol. 6 g of the ion exchanger loaded with esterase are stirred for 72 hours at room temperature with 6 g of oleic acid and 1.0 g of ethanol. The catalyst is then filtered off. The determination of the acid number and the ester number gives a degree of esterification of 81.1%.

It will be understood that the specification and examples are illustrative but not limitative of the present invention and that other embodiments within the spirit and scope of the invention will suggest themselves to those skilled in the art.

We claim:

1. In the enzyme-mediated synthesis of an ester or lactone of at least one carboxylic acid of the formula

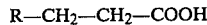

R—CH₂—CH₂—COOH wherein
R is a hydrogen atom, or a hydrocarbon radical which has 1 to 21 carbon atoms and which can be substituted by hydroxyl groups or alkoxyl groups with 1 to 10 carbon atoms, wherein such acid is reacted with at least one primary or secondary alcohol having from 1 to 15 carbon atoms in the presence of an esterase derived from Mucor miehei the improvement comprising effecting the reaction in the absence of water other than that formed in the reaction.

2. A process according to claim 1, wherein the synthesis is effected at a temperature from about 0° to 50° C.

3. A process according to claim 1, wherein the mol ratio of carboxylic acid to alcohol is from about 2:1 to 1:6.

4. A process according to claim 1, wherein the enzyme is used in a quantity of about 1 to 30% by weight of the carboxylic acid.

5. A process according to claim 1, wherein the synthesis is effected at about room temperature, the mol ratio of carboxylic acid to alcohol is from about 1:1 to 1:1.1, and the enzyme is used in a quantity of about 3 to 20% by weight of the carboxylic acid.

* * * * *